(12) United States Patent
Kunst et al.

(10) Patent No.: US 7,253,337 B2
(45) Date of Patent: Aug. 7, 2007

(54) GENE REGULATORY REGION THAT PROMOTES EARLY SEED-SPECIFIC TRANSCRIPTION

(75) Inventors: Ljerka Kunst, Vancouver (CA); Mark Andrew Smith, Vancouver (CA); Hangsik Moon, Vancouver (CA)

(73) Assignee: The University of British Columbia, Vancouver, British Columbia ( * ) Notice: Subject to any disclaimer, the term of this patent is extended or adjusted under 35 U.S.C. 154(b) by 365 days.

(21) Appl. No.: 10/276,976

(22) PCT Filed: May 24, 2001

(86) PCT No.: PCT/IB01/01131

§ 371 (c)(1),
(2), (4) Date: Aug. 5, 2003

(87) PCT Pub. No.: WO01/90386

PCT Pub. Date: Nov. 29, 2001

(65) Prior Publication Data

US 2004/0049811 A1    Mar. 11, 2004

Related U.S. Application Data

(60) Provisional application No. 60/206,787, filed on May 24, 2000.

(51) Int. Cl.
*C12N 15/82* (2006.01)

(52) U.S. Cl. .................. 800/287; 536/24.1; 435/320.1; 435/419; 435/468; 435/469

(58) Field of Classification Search ............... 536/24.1; 435/320.1, 419, 468, 469
See application file for complete search history.

(56) References Cited

U.S. PATENT DOCUMENTS 5,623,067 A * 4/1997 Vandekerckhove et al. ........................ 536/24.1
6,100,450 A * 8/2000 Thomas et al. ............. 800/287

OTHER PUBLICATIONS

Kim Y. et al. A 20 nucleotide upstream element is essential for the nopaline synthase (nos) promoter activity. Plant Mol Biol. Jan. 1994;24(1):105-17.*
De Boer G. et al. Sequences surrounding the transcription initiation site of the Arabidopsis enoyl-acyl carrier protein reductase gene control seed expression in transgenic tobacco. Plant Mol Biol. Apr. 1999;39(6):1197-207.*

* cited by examiner

*Primary Examiner*—Cynthia Collins
(74) *Attorney, Agent, or Firm*—Morgan Lewis & Bockius LLP

(57) ABSTRACT

Nucleic acid sequence capable of regulating transcription during embryogenesis in plants is provided. This sequence may be used in transgenic plants to promote high levels of expression of foreign and endogenous genes in developing seeds to affect seed lipid metabolism, protein or carbohydrate composition and accumulation, or seed development. In addition, these sequences may be useful for the production of modified seed containing novel recombinant proteins which have pharmaceutical, industrial or nutritional value, or novel products like plastics.

14 Claims, 1 Drawing Sheet

Figure 1. *Lesquerella fendleri LfKCS3* promoter:

(Length: 573 bp)

```
                                    GAA TTCGGAAATG GGCCAAGTGA  -573
AATGGAAATA GAGCTTCAAT CCATTTAGTC CCACTCAAAA TGGTGCTCGA  -550
ATTATATTTA GTTACGTTCG AATCAGACAA CCAAGTATTT GGTTAATAAA  -500
AACCACTCGC AACAAAGGAA AAACACCAAG CGCGTGCGTC AACATCCGA   -450
CGGAAGGGGG GTAATGTGGT CCGAAAACCT TACAAAAATC TGACGTCATC  -400
TACCCCCGAA AACGTTGAAT CGTCAACGGG GGTAGTTTTC GAATTATCTT  -350
TTTTTTAGGG GCAGTTTTAT TAATTTGCTC TAGAAATTTT ATGATTTTAA  -300
TTAAAAAAAG AAAAAGAATA TTTGTATATT TATTTTTTAT ACTCTTTTTT  -250
TGTCCAACTA TTTCTCTTAT TTTGGCAACT TTAACTAGAC TAGTAACTTA  -200
TGTCAATGTG TATGGATGCA TGAGAGTGAG TATACACATG TCTAAATGCA  -150
TGCCTTATGA AAGCAACGCA CCACAAAACG AAGACCCCTT TACAAATACA  -100
TCTCATCCCT TAGTACCCTC TTACTACTGT CCCGACACAA ACTCAAAACA  -50
ATGACATCTCTAAAC
```

GENE REGULATORY REGION THAT PROMOTES EARLY SEED-SPECIFIC TRANSCRIPTION

This application derives priority from U.S. Provisional Patent Application No. 60/206,787, which was filed May 24, 2000.

FIELD OF THE INVENTION

This invention relates to a nucleic acid sequence, which regulates transcription during embryogenesis in plants. More specifically, the nucleic acid sequence of the present invention can be used in transgenic plants to promote high levels of expression of foreign and endogenous genes in developing seeds to affect seed lipid metabolism, protein or carbohydrate composition and accumulation, or seed development. In addition, the nucleic acid sequence of the present invention can be useful for the production of modified seed containing novel recombinant proteins which have pharmaceutical, industrial or nutritional value, or novel products like plastics.

BACKGROUND

Most of the information about seed-specific gene expression comes from studies of genes encoding seed storage proteins like napin, a major protein in the seeds of *Brassica napus*, or conglycinin of soybean. Furthermore, upstream DNA sequences directing strong embryo-specific expression of these storage proteins have been used successfully in transgenic plants to manipulate seed lipid composition and accumulation (Voelker et al., 1996). However, expression of storage protein genes begins fairly late in embryogenesis. Thus, promoters of seed storage protein genes may not be ideal for all seed-specific applications. For example, storage oil accumulation commences significantly before the highest level of expression of either napin (Stalberg et al., 1996) or conglycinin (Chen et al., 1988) is achieved. It is, therefore of interest to identify other promoters which control expression of genes in developing embryos with temporal specificity different from that of seed storage proteins.

SUMMARY OF THE INVENTION

The nucleic acid sequence of the present invention can be used to regulate transcription during embryogenesis in plants. By the present invention it is possible to promote high levels of expression of foreign and endogenous genes in developing seeds to affect seed lipid metabolism, protein or carbohydrate composition and accumulation, or seed development. The present invention can also be useful for the production of modified seed, which contains novel recombinant proteins.

BRIEF DESCRIPTION OF THE DRAWING

The FIGURE shows nucleic acid sequence (SEQ ID NO: 1) of the insert in the plasmid pLfKCS3-GUS.

DETAILED DESCRIPTION

The inventors have determined that a more suitable gene regulatory region for directing gene expression aimed at seed oil modification would originate from a seed lipid metabolic gene expressed in a seed-specific manner. One such gene is LfKCS3, which encodes a condensing enzyme of very long chain fatty acid biosynthesis in *Lesquerella fendleri*. LfKCS3 condensing enzyme is thought to be localized in the endoplasmic reticulum where it catalyzes the sequential elongation of C18 fatty acyl chains to C20 in length. RNA blot analyses showed that the LfKCS3 gene transcript was present only in developing embryos. The inventors isolated the 5' regulatory region of the LfKCS3 gene and in the present application demonstrate that it is useful in promoting early seed-specific transcription of heterologous genes in *Arabidopsis*. Regulatory 5' DNA sequences promoting early seed-specific transcription found upstream of other plant KCS genes have also been isolated and disclosed previously (U.S. Provisional Patent Application filed Aug. 4, 1999, Inventors Kunst and Clemens).

Plasmid pLfKCS3-GUS was deposited in GenBank (http://www.ncbi.nlm.nih.gov/entrez/query.fcgi?db=Nucleotide) on Dec. 27, 2001 and can be found as *Lesquerella fendleri* 3-ketoacyl-CoA synthase (KCS3) gene under the Accession No. AF367052.

Isolated transcription regulatory region from the LpfKCS3 gene is capable of directing expression of desired genes at an early stage of development in a seed-specific manner. Because this regulatory sequence can also promote transcription in developing seeds of a different plant species, it can be used in a variety of dicotyledonous plants for modification of the seed phenotype.

Examples of applications wherein the nucleic acid sequence of the present invention can be useful include, for example:

(1) altered seed fatty acid compositionor seed oil composition and accumulation, (2) altered seed protein or carbohydrate composition or accumulation, (3) enhanced production of desirable seed products, (4) suppression of production of undesirable seed products using antisense, co suppression or ribozyme technologies, (5) production of novel recombinant proteins for pharmaceutical, industrial or nutritional purposes, (6) production of novel compounds/products in the seed, ie. secondary metabolites, plastics, etc.

The methods employed in the isolation of the nucleic acid of the present invention and the uses thereof are discussed in the following non-limiting examples:

EXAMPLES

Isolation of a Seed-Specific Promoter Region form *Lesquerella fendleri* A *Lesquerella fendleri* genomic DNA library was obtained from Dr. Chris Somerville, Carnegie Institution of Washington, Stanford, Calif. The genomic library was plated on *E. coli* LE392 (Promega) and about 150,000 clones were screened using *Arabidopsis* FAE1 gene (James et al., 1995) as a probe. The probe was prepared by PCR using pGEM7-7Zf(+)-FAE1 (Millar and Kunst, 1997) as a template with FAE1 upstream primer (SEQ ID NO: 2); 5'-CCGAGCTCAAAGAGGATACATAC-3'(SEQ ID NO: 2) and FAE1 downstream primer (SEQ ID NO: 3). 5'-GATACTCGAGAACGTTGGCACTCAGATAC-3'(SEQ ID NO: 3). PCR was performed in a 10 µl reaction containing 10 ng of the template, 2 mM $MgCl_2$, 1.1 µM of each primer, 100 µM of (dCTP+dGTP+dTTP) mix, 50 µCi of [$\alpha$-32P]dATP, 1×PCR buffer and 2.5 units of Taq DNA polymerase (Life Technologies). Amplification conditions were: 2 min of initial denaturation at 94° C., 30 cycles of 94° C. for 15 sec, 55° C. for 30 sec, 72° C. for 1 min and 40 sec, followed by a final extension at 72° C. for 7 min. The amplified radiolabeled probe was purified by QIAquick PCR Purification Kit (Qiagen) and denatured by boiling before adding to the hybridization solution. Hybridization took place overnight at 65° C. in a solution containing 6×SSC, 20 mM $NaH_2PO_4$. 0.4% SDS, 5×Denhardt's solution, and 50 µg/ml sonicated, denatured salmon sperm DNA (Sigma) and washing was performed three times for 20 min each in 2×SSC, 0.5% (w/v) SDS at 65° C.

Nine clones with sequences corresponding to the *Arabidopsis* FAE1 gene were isolated from the *Lesquerella fendleri* genomic library. The phage DNA from those nine clones was extracted and purified using QIAGEN Lambda Mini Kit (Qiagen) according to the manufacturer's protocol. One of them was digested with EcoRI and a 4.3 kb fragment was subcloned into the pGEM-7Zf(+) vector (Promega) cut with EcoRI, resulting in the vector pMHS15. The whole insert was sequenced with ABI automatic 373 DNA sequencer using fluorescent dye terminators. Approximately 573 bp of the 5' upstream region of the 4.3 kb genomic DNA was amplified using the high fidelity Pfu polymerase (Stratagene) with a forward primer (SEQ ID NO: 4)5'-CG-CAAGCTTGAATTCGGAAATGGGCCAAG-3'(SEQ ID NO: 4) and a reverse primer (SEQ ID NO: 5)5'-CGCGTC-GACTGTTTTGAGTTTGTGTCGGG-3'(SEQ ID NO: 5). The amplified fragment was inserted upstream of the GUS gene in pBI101 (Clontech) cut with HindIII and SalI, resulting in the vector pLfKCS3-GUS. The sequence of the insert in the plasmid pLfKCS3-GUS is shown in FIG. 1 (SEQ ID NO: 1) (SEQ ID NO: 1).

Functional Analysis of the LfKCS3 5' Upstream Region

To evaluate the ability of the 5' upstream fragment of the LfKCS3 gene to confer seed-specific and temporal regulation of gene expression in plants, the pLfKCS3-GUS construct was introduced into *Agrobacterium tumefaciens* strain GV3101 (pMP90) (Koncz and Schell, 1986) by heat-shock and selected for resistance to kanamycin (50 µg/mL). *A. thaliana* ecotype Columbia was transformed with *A. tumefaciens* harbouring the pLfKCS3-GUS construct using floral dip method (Clough and Bent, 1998). Screening for transformed seed was done on 50 µg/mL kanamycin as described previously (Katavic et al., 1994). Approximately 100 transgenic lines were generated for each construct.

Histochemical localization of GUS activity in transgenic plants was done on tissue sections as follows. Sections were incubated in 50 mM sodium phosphate, pH 7.0, 0.5 mM potassium ferricyanide, 0.5 mM potassium ferrocyanide, 10 mM EDTA, 0.05%(w/v) triton X-100, and 0.35 mg/ml 5-bromo-4-chloro-3-indolyl-β-D-glucuronide (X-Gluc) for 4 to 7 hours at 37° C. (Jefferson, 1987). Following staining the blue-stained samples were fixed in 70°/ethanol.

Using this assay, over 30 independent transgenic *Arabidopsis* lines were examined for the embryo-specific expression of the GUS gene. In addition, leaves, stems, inflorescences, roots, and siliques at different stages of development were histochemically stained for β-glucuronidase activity. The GUS reporter gene fused to the LfKCS3 promoter was not expressed in any of the vegetative tissues, whereas it was highly expressed in developing embryos. We also compared the LfKCS3 promoter with the LFAH12 promoter that was reported to be an early and seed-specific promoter active already at the torpedo stage of *Arabidopsis*(Broun et al., 1998). Our results suggest that the LfKCS3 promoter is active even earlier. Thus, the onset of the LfKCS3 promoter activity coincides with or precedes that of storage oil accumulation. GUS activity in all the examined transgenic lines persisted throughout subsequent embryo development. Thus the LfKCS3 promoter is useful for seed-specific expression of foreign genes in transgenic plants.

In conclusion, we have demonstrated that the elements which confer both tissue specific and developmental regulation of a reporter gene linked to the LfKCS3 promoter reside within the 573 bp upstream of the AUG translation initiation codon. Our experiments also show that the *Lesquerell afenaleri* LfKCS3 promoter directs seed-specific expression at least as early as the torpedo stage embryo and that the it is capable of promoting transcription in plants other than *Lesquerell afendleri*.

It should also be mentioned that the seed-specific expression conferred by the LfKCS3 promoter is independent of the native terminator at the LfKCS3 gene 3' end. In all our constructs, a terminator derived from the *Agrobacterium*nopaline synthase gene was used. Thus, the sequence in the 573 bp promoter construct is sufficient for the desired expression profile independent of ancillary sequences.

REFERENCES

Broun, P., Boddupalli, S., and Somerville, C. (1998) A bifunctional oleate 12-hydroxylase: desaturase from *Lesquerell afendleri*. Plant J. 13, 201-210

Chen, Z. L., Pan, N. S., and Beachy, R. N. (1988) A DNA sequence element that confers seed-specific enhancement to a constitutive promoter. EMBO J. 6: 3559-3564.

Clough, S. J. and Bent, A. F. (1998) Floral dip: a simplified method for *Agrobacterium*-mediated transformation of *Arabdiopsis thaliana*. Plant J. 16: 735-743.

James, D. W., Jr., Lim, E., Keller, J., Plooy, I., Ralston, E., and Dooner, H. K. (1995) Directed tagging of the *Arabidopsis* FATTY ACID ELONGATION(*FAE*1) gene with the maize transposon *Activator*. Plant Cell 7: 309-319.

Jefferson, R. A., Kavanaugh, T. and Bevan, M. W. (1987) GUS fusions: β-glucuronidase as a sensitive and versatile gene fusion marker system in higher plants. EMBO J. 6: 3901-3907.

Katavic, V., Haughn, G. W., Reed, D., Martin, M., and Kunst, L. (1994) In planta transformation of *Arabidopsis thaliana* Mol. Gen. Genet. 245: 363-370.

Koncz, C. and Schell, J. (1986) The promoter of $T_L$-DNA gene 5 controls the tissue-specific expression of chimaeric genes carried by a novel type of *Agrobacterium*binary vector. Mol. Gen. Genet. 204: 383-396.

Stalberg, K., Ellerstoem, M., Ezcurra, I., Ablov, S., and Rask, L. (1996) Disruption of an overlapping e-box-ABRB motif abolished high transcription of the napA storage-protein promoter in transgenic *Brassica napus* seeds. Planta 199: 515-519.

Voelker, T. A., Hayes, T. R., Cranmer, A. M., Turner, J. C., and Davies H. M. (1996) Genetic engineering of a quantitative trait: Metabolic and genetic parameters influencing the accumulation of laurate in rapeseed. Plant J. 9: 229-241.

What we claim is:

1. An isolated nucleic acid comprising a promoter for directing seed-specific transcription of genes in plants, wherein the nucleic acid comprises SEQ ID NO: 1.

2. The nucleic acid of claim 1, wherein the nucleic acid consists of SEQ ID NO: 1.

3. A vector comprising the nucleic acid of claim 1.

4. The vector of claim 3 wherein the vector is a plasmid.

5. The plasmid of claim 4 wherein the plasmid is carried by *Agrobacterium tumefaciens*.

6. The plasmid of claim 4 wherein the plasmid is pLfKCS3-GUS.

7. A transformed plant cell comprising a nucleic acid of claim 1.

8. The plant cell of claim 7 wherein the plant cell comprises a cell from *Arabidopsis thaliana*.

9. A method of transforming a plant cell comprising the steps of
   a) providing an isolated nucleic acid comprising a promoter for directing seed-specific transcription of genes in plants, wherein the nucleic acid comprises SEQ ID NO: 1;
   b) inserting the nucleic acid into a vector; and
   c) inserting the vector into a plant cell.

10. The method of claim 9 wherein the step of inserting the vector into a plant cell comprises introduction of the vector in *Agrobacterium tumefaciens* followed by contacting the plant cell with the *Agrobacterium tumefaciens* for a time and under conditions sufficient to allow transformation.

11. The method of claim 9 wherein the vector comprises a plasmid.

12. The method of claim 11 wherein the plasmid comprises pLfKCS3-GUS.

13. The method of claim 10 wherein the vector comprises a plasmid.

14. The method of claim 13 wherein the plasmid comprises pLfkCS3-GUS.

* * * * *

SEQUENCE LISTING

<160> NUMBER OF SEQ ID NOS: 5

<210> SEQ ID NO 1
<211> LENGTH: 588
<212> TYPE: DNA
<213> ORGANISM: Lesquerella fendleri

<400> SEQUENCE: 1

| | | | | | |
|---|---|---|---|---|---|
| gaattcggaa | atgggccaag | tgaaatggaa | atagagcttc | aatccattta | gtcccactca | 60 |
| aaatggtgct | cgaattatat | ttagttacgt | tcgaatcaga | caaccaagta | tttggttaat | 120 |
| aaaaaccact | cgcaacaaag | gaaaaacacc | aagcgcgtgc | gtccaacatc | cgacggaagg | 180 |
| ggggtaatgt | ggtccgaaaa | ccttacaaaa | atctgacgtc | atctaccccc | gaaaacgttg | 240 |
| aatcgtcaac | gggggtagtt | ttcgaattat | cttttttta | ggggcagttt | tattaatttg | 300 |
| ctctagaaat | tttatgattt | taattaaaaa | aagaaaaaga | atatttgtat | atttattttt | 360 |
| tatactcttt | ttttgtccaa | ctatttctct | tattttggca | actttaacta | gactagtaac | 420 |
| ttatgtcaat | gtgtatggat | gcatgagagt | gagtatacac | atgtctaaat | gcatgcctta | 480 |
| tgaaagcaac | gcaccacaaa | acgaagaccc | ctttacaaat | acatctcatc | ccttagtacc | 540 |
| ctcttactac | tgtcccgaca | caaactcaaa | acaatgacat | ctctaaac | | 588 |

<210> SEQ ID NO 2
<211> LENGTH: 23
<212> TYPE: DNA
<213> ORGANISM: Artificial Sequence
<220> FEATURE:
<223> OTHER INFORMATION: FAE1 PCR Primer

<400> SEQUENCE: 2
ccgagctcaa agaggataca tac                                               23

<210> SEQ ID NO 3
<211> LENGTH: 29
<212> TYPE: DNA
<213> ORGANISM: Artificial Sequence
<220> FEATURE:
<223> OTHER INFORMATION: FAE1 PCR Primer

<400> SEQUENCE: 3
gatactcgag aacgttggca ctcagatac                                         29

<210> SEQ ID NO 4
<211> LENGTH: 29
<212> TYPE: DNA
<213> ORGANISM: Artificial Sequence
<220> FEATURE:
<223> OTHER INFORMATION: PCR Primer

<400> SEQUENCE: 4
cgcaagcttg aattcggaaa tgggccaag                                         29

<210> SEQ ID NO 5
<211> LENGTH: 29
<212> TYPE: DNA
<213> ORGANISM: Artificial Sequence
<220> FEATURE:
<223> OTHER INFORMATION: PCR Primer

<400> SEQUENCE: 5
cgcgtcgact gttttgagtt tgtgtcggg                                         29